United States Patent [19]

Deckelbaum et al.

[11] Patent Number: 4,981,138
[45] Date of Patent: Jan. 1, 1991

[54] ENDOSCOPIC FIBEROPTIC FLUORESCENCE SPECTROMETER

[75] Inventors: Lawrence I. Deckelbaum, Woodbridge; Cyrus R. Kapadia, Guilford; Kenneth M. O'Brien, Cheshire; Mark L. Stetz, Branford, all of Conn.

[73] Assignee: Yale University, New Haven, Conn.

[21] Appl. No.: 213,414

[22] Filed: Jun. 30, 1988

[51] Int. Cl.[5] .............................................. A61B 6/00
[52] U.S. Cl. .................................................... 128/665
[58] Field of Search ............... 128/633, 634, 664, 665, 128/303.1

[56] References Cited

U.S. PATENT DOCUMENTS

| | | | |
|---|---|---|---|
| 4,213,462 | 7/1980 | Sato | 128/634 |
| 4,556,057 | 12/1985 | Hiruma et al. | 128/634 |
| 4,641,650 | 2/1987 | Mok | 128/665 |
| 4,648,892 | 3/1987 | Kittrell et al. | 128/634 |
| 4,718,417 | 1/1988 | Kittrell et al. | 128/634 |
| 4,768,513 | 9/1988 | Juzuki | 128/634 |
| 4,785,806 | 11/1988 | Deckelbaum | 128/634 |

OTHER PUBLICATIONS

"Clinical Measurement of Tumor Fluorescence Using a New Diagnostic System With Hematoporphyrin Derivative, Laser Photoradiation, and a Spectroscope", Kato et al, Laser in Surgery and Medicine 4:49–58 (1984).

"Laser Induced Fluorescence Spectroscopy from Native Cancerous and Normal Tissue", Alfano et al, IEEE Journal of Quantum Electronics, vol. QE-20, No. 12, Dec. 1984, pp. 1507–1511.

"Fluorescence Spectra from Cancerous and Normal Human Breast and Lung Tissues", Alfano et al, IEEE Journal of Quantum Electronics, vol. QE 23, No. 10, Oct. 1987.

Primary Examiner—Kyle L. Howell
Assistant Examiner—John C. Hanley
Attorney, Agent, or Firm—Darby & Darby

[57] ABSTRACT

A method of detecting pre-malignant lesions in the gastrointestinal tract comprises positioning an opitcal fiber in a patient's gastrointestinal tract and transmitting ultraviolet laser light through said optical fiber means to cause the tissue of the gastrointestinal tract illuminated by the laser to fluoresce in the near visible band of frequencies. The fluorescence spectrum is returned through the optical fiber to a spectrum analyzing means which analyzes the spectrum in the wavelength range of 350 to 700 nm to determine whether the tissue caused to fluoresce is pre-malignant. Tissue so diagnosed may be ablated by a high power laser using the same fiberoptic system.

6 Claims, 2 Drawing Sheets

ENDOSCOPIC FIBEROPTIC FLUORESCENCE SPECTROMETER

This invention was made with Government support under Grant No. HL-36723 awarded by The National Institutes of Health. The Government has certain rights in the invention.

This invention relates to laser spectroscopy. More particularly, this invention relates to a fluorescence spectrometer that can be used to detect pre-cancerous conditions.

BACKGROUND OF THE INVENTION

It is highly desirable to detect malignancies in human tissue at the earliest possible date. Certain types of tissue when changing from normal to malignant, pass through an intermediate stage in which the tissue cells are not actually malignant but have a strong potential to become malignant. Such pre-malignant states are well known to exist in the gastrointestinal tract (i.e., esophagus, stomach and colon). Surveillance examinations are now more or less routinely performed to detect both pre-malignant and early malignant conditions.

Currently, the preferred diagnostic method for examining the gastrointestinal tract involves the use of an endoscope to detect polyps or malignant lesions at an early stage. In the colon for instance, it is now known that most if not all malignancies arise in pre-existent polyps. Polyps may be hyperplastic, adenomatous or malignant. Hyperplastic polyps consist of normal tissue and are therefore benign. Adenomatous polyps consist of abnormal tissue but are believed to be precursors of malignant tumors. With currently available techniques, it is often necessary to remove the polyp by biopsy or, if necessary, surgery.

Thus, there is a need for a reliable diagnostic procedure that would enable medical personnel to determine instantaneously the nature of such polyps and other pre-malignant lesions of the gastrointestinal tract and other parts of the body.

It is well-known that laser induced fluorescence can be used to distinguish normal from abnormal tissue. Fluorescence spectroscopy has been used in the gastrointestinal tract to detect cancerous conditions but, in the past, this has involved pre-treatment with a fluorescent agent (i.e., hematoporphyrin derivative) which causes tissue to fluoresce. However, hematoporphyrin derivative causes side effects which greatly reduce its utility for clinical purposes. The present invention provides a laser induced fluorescence spectroscopic system which does not require the administration of any exogenous agent to induce fluorescence and which can be used with an optical fiber inserted through a conventional endoscope to examine the surface of the colon or other gastrointestinal viscus and reliably distinguish adenomatous from normal tissue.

SUMMARY OF THE INVENTION

In accordance with the invention, ultraviolet laser energy is transmitted through an optical fiber onto the surface of the patient's tissue under examination. The ultraviolet light causes the tissue to fluoresce in the visible wavelengths, e.g., 350–700 nanometers (nm). By examining the spectra of the fluorescence produced it is possible to diagnose the type of tissue with a degree of reliability greater than that which can be achieved by visual inspection.

THE DRAWINGS

DETAILED DESCRIPTION

Figure 1:
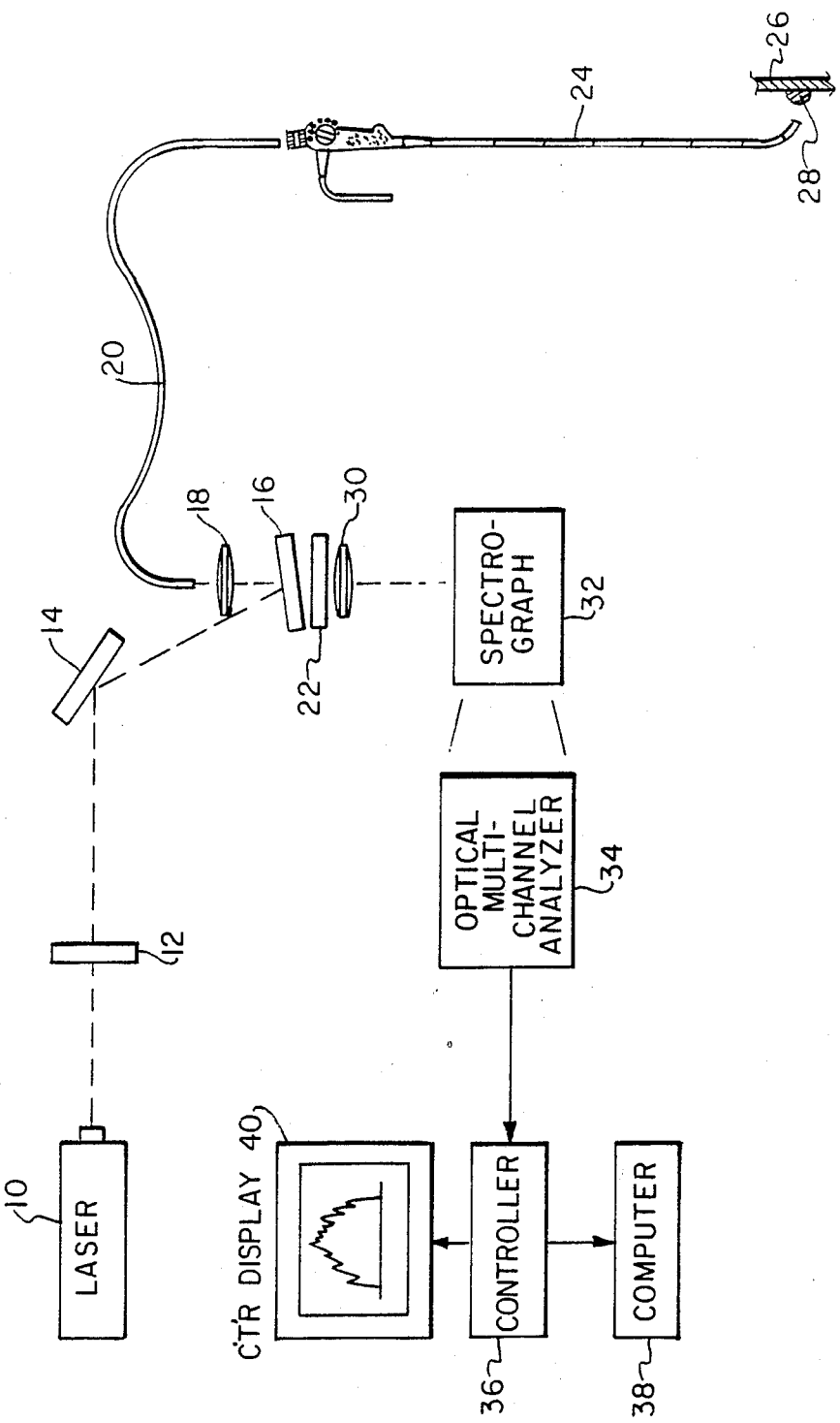
FIG. 1 is a block diagram showing the invention as it would be used in the gastrointestinal tract.

FIG. 1 shows in block diagram form a preferred embodiment of the invention used experimentally for diagnosing pre-malignancies in the gastrointestinal tract.

Referring to FIG. 1, the ultraviolet light from a helium-cadmium laser 10 is filtered by an ultraviolet transmitting filter 12 to remove the blue plasma lines of the laser. These are wavelengths above 350 nm. The laser beam is reflected by mirror 14 to a beam splitter 16. Beam splitter 16 may be a conventional device, for example comprising an aluminum (mirror) spot on a quartz window. The mirrored spot reflects the laser ultraviolet energy through a lens 18 into a single fiber 20. Fiber 20 may be inserted through the biopsy channel of a standard endoscope 24 of the type which can be inserted into the patient's colon.

Part of the surface of the colon (for example) is shown diagrammatically at 26 with the tissue to be diagnosed shown as a polyp 28. Such polyps, which are relatively common, may be benign, pre-malignant (adenomatous) or malignant.

As the endoscope 24 is positioned within the colon, the low power laser 10 illuminates the tissue to produce endogenous fluorescence which is collected and transmitted by fiber 20 through beam splitter 16, an ultraviolet blocking filter 22, and an achromatic lens 30 which focuses the fluorescence onto a spectrograph 32. The ultraviolet blocking filter 22 prevents light from laser 10 from reaching spectrograph 32. The spectrograph 32 disperses the light according to wavelength and images the optical spectrum onto an optical multichannel analyzer 34. Analyzer 34 produces a multi-channel electrical output that represents the fluorescence spectrum in analog form. These analog signals (each corresponding to a portion of the spectrum) are converted to a corresponding multiplicity of digital signals by a controller 36 and transmitted to a computer 38 and CRT display 40 which displays the fluorescence spectrum of polyp 32.

The optical multichannel analyzer 34 may comprise a linear diode array (for example, Princeton Instruments Model No. IR 4700) including 1,024 photocells coupled to a microchannel plate intensifier. Less than all of the photocells may be used for a particular application. The parallel photocell signals are coupled to the controller 36 (Princeton Instruments Model No. ST 100) which interfaces with the computer 38. Standard techniques may be used to improve signal-to-noise ratio and to correct for background fluorescence or other extraneous signals. The computer 36 is programmed to distinguish fluorescence spectra characteristic of pre-malignant or malignant tissue from spectra characteristic of normal tissue. Calibration for wavelength and intensity may be accomplished by comparison with frequency spectra obtained from a mercury vapor lamp, and an NBS traceable calibrated tungsten halogen lamp.

RECOGNITION OF ADENOMATOUS TISSUE

Human tissue from the gastrointestinal tract may be classified as normal, hyperplastic, adenomatous or malignant. Examination of such tissue has shown that adenomatous tissue emits a characteristic endogenous fluorescence that is distinct from that emitted by normal colonic mucous or hyperplastic polyps. Ultraviolet wavelengths are preferred as an illuminating source because they stimulate more visible fluorescence than in longer wavelengths which means that more visible information is contained in the patterns. As one example, using a helium-cadmium laser (Omnichrome Model 356-5MS; 10 mw continuous wave power at a wavelength of 325 nm, beam diameter 0.9 mm), the fluorescence spectra shown in FIG. 2 were produced, curve 42 representing the average fluorescence pattern for normal tissue, curve 44 the average pattern for hyperplastic tissue, and curve 46 the average pattern for adenomatous tissue.

Figure 2:
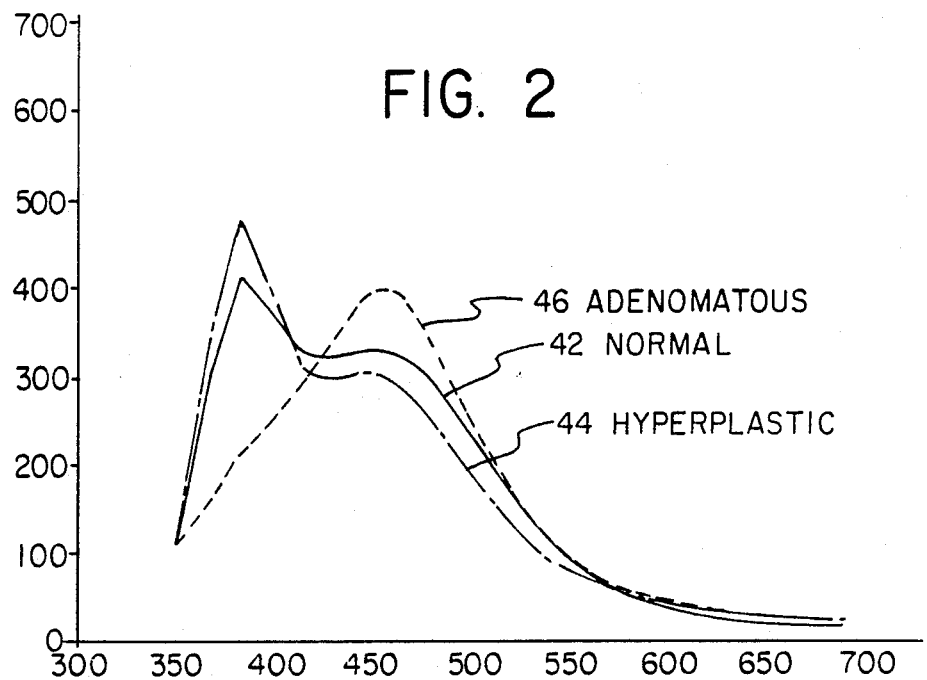
FIG. 2 is a graph showing the average fluorescence spectra of hyperplastic, adenomatous and normal colonic tissue.

The fluorescence spectra in FIG. 2 were derived from in vitro experiments with each curve representing an average of a multiplicity of curves. These curves indicate that the normal and hyperplastic tissues are very similar but that the spectrum for adenomatous tissue differs markedly. The curves also indicate that by examining the wavelength range of 350 to 500 nm adenomatous tissue can be discriminated reliably from either normal or hyperplastic tissue. Currently, it appears that the most important range for diagnostic purposes is the range of 350 to 400 nm. Experimentally, by comparing fluoescence intensities at 350 nm, 366 nm, 382 nm, and 398 nm, accurate identification of adenomatous tissue has been achieved in 92–97% of the cases studied. Other organs (e.g., lung, bladder, prostate) are likely to have other characteristic patterns.

Based on experimental observations, it is also known that malignant tissue can be discriminated from normal and/or hyperplastic tissue. It is anticipated that the algorithms required to identify malignant lesions of the gastrointestinal tract will be developed but this information is not currently known. Moreover, while all adenomatous tissue is regarded as pre-malignant, there are other forms of pre-malignant tumors which are not adenomatous but which also may produce characteristic fluorescence spectra that would enable their identification and discrimination from normal tissue.

More precise discrimination between normal and adenomatous or malignant tissue is possible using computer aided regression analysis of the fluorescence spectra. For example, a laser induced fluorescence (LIF) score can be derived by stepwise multivariate regression analysis to distinguish the normal or hyperplastic tissue from adenomatous tissue based on the fluorescence intensities of selected wavelengths. Other linear and non-linear pattern recognition algorithms may similarly be employed.

There are known ways to recognize the patterns which typify pre-malignant and normal tissue (for example, computer aided) and the invention contemplates the use of any technique which enables reliable discrimination between the normal and abnormal tissues.

Figure 3:
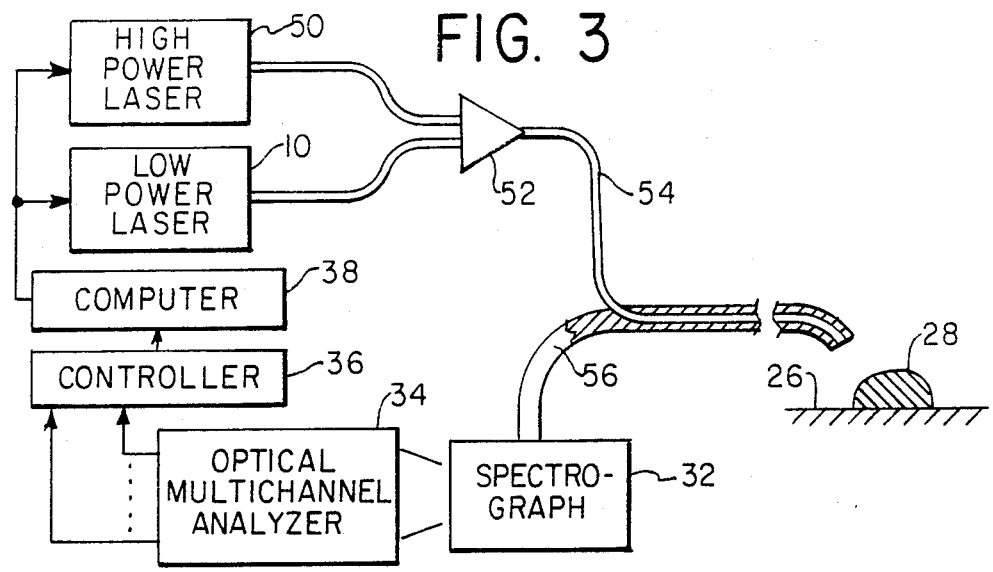
FIG. 3 is a block diagram showing an embodiment of the invention used in conjunction with a high power laser for ablation of abnormal tissue.

Because the invention provides an instantaneous diagnostic procedure, it is contemplated that the invention may be incorporated into an apparatus which can ablate (vaporize) abnormal tissue after it has been diagnosed in accordance with the invention. FIG. 3 shows such a system with the numerals used in FIG. 1 being used to designate like components.

In FIG. 1, a high power laser 50 provides the energy to ablate the pre-malignant (or malignant) tissue. A low power ultraviolet laser 10 is used to cause fluorescence. As explained below, a single laser may provide the functions of the two lasers 10 and 50. The outputs of lasers 10 and 50 are coupled through a fiberoptic coupler 52 to an optical fiber 54. The fluorescence spectra are returned to spectrograph 32 by a fiber 56 which together with fiber 54 may be inserted through an endoscope into the gastrointestinal tract (e.g., the colon) of a patient. One or more fibers 56 may be used. The fibers 54 and 56 each comprise a silica based optical fiber or other material that transmits the wavelengths of interest with minimal loss of optical energy within the fiber. The fiber(s) 56 and fiber 54 can be replaced by a single fiber and beam splitter as shown in FIG. 1.

The computer 38 is programmed to generate a control signal that causes the high power laser 50 to fire when the distal end of fiber 54 is aimed at polyp 32 if computer 38 indicates that the polyp is pre-maligant. After completion of ablation, the fluorescence pattern changes from "abnormal" to "normal" and inhibits further firing of the high power laser 50.

It is desirable to ablate the abnormal polyps 32 in such a way as to avoid charring. If charring occurs, the fluorescence pattern is obscured and the system may therefore be unable to distinguish between pre-malignant or malignant tissue and normal tissue. The laser ablation system of FIG. 3 avoids this serious drawback by a combination of features including the wavelength and energy parameters of the laser.

THE HIGH POWER LASER

Charring is dependent upon the wavelength and peak power density of the high power laser 50. Peak power density may be defined as peak power per unit area, where peak power is equal to the pulse energy divided by pulse duration. At any wave-length, charring will not occur if peak power density exceeds a threshold which is inversely proportional to the absorption of laser energy by the tissue. Tissue absorption in turn is dependent on wavelength. Thus, increasing wavelength from the ultraviolet through the visible range decreases tissue absorportion which raises the threshold. It is necessary that there be a balance between the peak power density and wavelength to achieve the desired result since if peak power density is too high, it is difficult, if not impossible, to tranmit the laser energy through an optical fiber. At ultraviolet and mid-infrared frequencies, silica fibers can conveniently be used to transmit the optical energy.

Ideally, all of the laser energy should be used to vaporize the lesion. To the extent the energy is not absorbed by tissue, it tends to heat the surrounding tissue, thereby increasing the likelihood of thermal damage. As pulse energy per unit area increases, the time required for ablation (and, therefore, the likelihood of thermal damage) decreases.

Currently, based on observations and theoretical conclusions, it is believed that ablation without charring is possible using a pulsed laser at a wavelength between 280 nm and 400 nm with a pulse duration of 10–500 ns wherein the pulse energy per unit area is greater than 20 $mJ/mm^2$. Good results in ablating atherosclerotic plaque have been obtained experimentally using a frequency-doubled, Q-switched Alexandrite laser (wavelength 378 nm, pulse duration 60 ns, repetition rate 28 Hz with pulse energy per unit area in the range of 50–96 mJ/mm$^2$). There was a marked decrease in the total energy required for ablation (and in the occurence of charring) when the pulse energy per unit area was greater than 35 mJ/mm$^2$. Satisfactory experimental results in ablating plaque have also been obtained with an excimer laser (308 or 351 nm) and a flashlamp pumped dye laser (450 nm).

Satisfactory experimental results in ablating plaque have also been achieved with laser energy at infrared frequencies. Specifically, an erbium: YAG laser (wavelength 2,940 nm, pulse duration 200 microseconds with pulse energy per unit area greater than 80 mJ/mm$^2$) and a holmium: YAG laser (wavelength 2,100 nm, pulse duration 100 microseconds, with pulse energy per unit area greater than 800 mJ/mm$^2$) have been used.

It is contemplated that a single laser may serve the functions of lasers 10 and 50. This would require that the single laser be switchable between high and low power outputs to alternately fluoresce and ablate.

THE FIBEROPTICS

The key factors in the fiberoptical system are (1) that the high power fiber 54 and the fluorescent sensing fibers 56 be directed at the same tissue; and (2) that the laser energy be coupled to the fiber 54 without causing fiber damage. A coaxial arrangement of fibers 56 about a central fiber 54 is advantageous as compared to other conventional fiber arrangements (e.g., hemispherical or random) since it is relatively easy to ensure that the outer fibers 56 are focused at the same point as the central high power fiber 54. It is also possible to use a single fiber for both the high power and lower power energy with suitable multiplexing devices (not shown) to direct the reflected fluorescent energy to the optical multichannel analyzer.

The fiberoptic coupler 52 must be capable of coupling the high and low power laser energy into the fiber 54 without damage. This requires precise alignment and a high precision connector of the type, for example, used for telecommunications. The fibers may be coated with a polymeric material chosen for mechanical durability and heat resistant characteristics. These coatings must also be free from attack by blood or other environmental fluids which they are likely to encounter and biocompatible with the environment.

OPERATION

The system may be arranged to ablate only when malignant or pre-malignant tissue is encountered or, alternatively, ablation may be inhibited only when normal tissue is detected. For example, when the fluorescence induced by the low power laser 10 indicates that the fiber 54 is directed at adenomatous or malignant tissue, a series of high power ablative pulses may be triggered from the high power laser 50. Following the series of pulses, a further fluorometric analysis may be used to assess for the residual presence of abnormal tissue. A further series of high power ablative pulses may be triggered until a fluorescence spectrum indicative of normal tissue is detected, at which point the catheter can be redirected (manually or automatically) until additional adenomatous or malignant tissue is detected. The alternative would be to continuously transmit high power ablative pulses which would be inhibited when normal tissue is sensed. Another mode of operation may entail manual control of the high power laser by the operator based on computer interpretation of the tissue fluorescence.

What is claimed is:

1. A method of detecting pre-malignant tissue, comprising positioning an optical fiber adjacent the tissue to be diagnosed, transmitting ultraviolet laser light through said optical fiber means to cause the tissue illuminated by said laser to fluoresce in the visible band of wavelengths, transmitting the fluorescence spectrum back through said optical fiber means to a spectrum analyzing means, and analyzing the spectrum at least in the wavelength range of 350 to 500 nm to determine whether the tissue caused to fluoresce is pre-malignant.

2. A method of detecting pre-malignant tissue in the gastrointestinal tract, comprising positioning an optical fiber means in a patient's gastrointestinal tract, passing ultraviolet laser light through said optical fiber means to cause the tissue of the gastrointestinal tract illuminated by said laser to fluoresce in the visible band of frequencies, transmitting the fluorescence spectrum back through said optical fiber means to a spectrum analyzing means, and analyzing the spectrum at least in the wavelength range of 350 to 500 nm to determine whether the tissue caused to fluoresce is pre-malignant.

3. A method of detecting pre-malignant tissue according to claim 2, wherein said optical fiber means is positioned by inserting it through an endoscope.

4. A method of ablating pre-malignant tissue in the gastrointestinal tract, comprising positioning an optical fiber means in a patient's gastrointestinal tract, passing ultraviolet laser light through said optical fiber means to cause the tissue of the gastrointestinal tract illuminated by said laser to fluoresce in the near visual band of frequencies, transmitting the fluorescence spectrum back through said optical fiber means to a spectrum analyzing means, analyzing the spectrum at least in the wavelength range of 350 to 500 nm to determine whether the tissue caused to fluoresce is pre-malignant, and ablating the tissue diagnosed as pre-malignant.

5. A method of ablating pre-malignant tissue in the gastrointestinal tract according to claim 4, wherein said optical fiber means is positioned by inserting it through an endoscope.

6. A method of ablating pre-malignant tissue in the gastrointestinal tract according to claim 5, wherein the tissue is ablated without charring.

* * * * *